(12) United States Patent
Que et al.

(10) Patent No.: US 9,121,027 B2
(45) Date of Patent: Sep. 1, 2015

(54) ENHANCED TRANSFORMATION OF RECALCITRANT MONOCOTS

(75) Inventors: Qiudeng Que, Cary, NC (US); David Nicholl, Apex, NC (US)

(73) Assignee: Syngenta Participations AG, Basel (CH)

( * ) Notice: Subject to any disclaimer, the term of this patent is extended or adjusted under 35 U.S.C. 154(b) by 576 days.

(21) Appl. No.: 13/455,751

(22) Filed: Apr. 25, 2012

(65) Prior Publication Data

US 2012/0278950 A1    Nov. 1, 2012

Related U.S. Application Data

(60) Provisional application No. 61/479,131, filed on Apr. 26, 2011.

(51) Int. Cl.
*C12N 15/82*    (2006.01)
*C12N 15/84*    (2006.01)
*C12N 9/90*    (2006.01)

(52) U.S. Cl.
CPC .............. *C12N 15/8205* (2013.01); *C12N 9/90* (2013.01); *C12N 15/821* (2013.01); *C12N 15/8245* (2013.01); *C12N 15/8246* (2013.01); *C12Y 503/01008* (2013.01)

(58) Field of Classification Search
None
See application file for complete search history.

(56) References Cited

U.S. PATENT DOCUMENTS

| | | | |
|---|---|---|---|
| 4,940,835 A | 7/1990 | Shah et al. | |
| 5,188,642 A | 2/1993 | Shah et al. | |
| 5,767,378 A | 6/1998 | Bojsen et al. | |
| 5,994,629 A | 11/1999 | Bojsen et al. | |
| 6,037,522 A | 3/2000 | Dong et al. | |
| 6,075,185 A | 6/2000 | Koziel et al. | |
| 6,531,648 B1 | 3/2003 | Lanahan et al. | |
| 6,858,777 B2 | 2/2005 | Zhong et al. | |
| 7,119,255 B2 * | 10/2006 | Betts et al. .................... | 800/287 |
| 2010/0192253 A1 | 7/2010 | Wu et al. | |

FOREIGN PATENT DOCUMENTS

WO    WO 2010/151634 A1    12/2010

OTHER PUBLICATIONS

Hoa et al. Plant Physiology 133: 161-169 (Sep. 2003).*
Rashid et al. Plant Cell Reports 15: 727-730 (1996).*
Jain et al. Plant Cell Reports 26: 581-590 (2007).*
International Search Report and Written Opinion, PCT/US12/34982, mailed Sep. 28, 2012.
Negrotto D et al. The use of phosphomannose-isomerase as a selectable marker to recover transgenic maize plants (*Zea mays* L.) via *Agrobacterium* transformation. Plant Cell Reports. 2000; 19: 798-803.
Wright M et al. Efficient biolistic transformation of maize (*Zea mays* L.) and wheat (*Triticum aestivum* L.) using the phosphomannose isomerase gene, pmi, as the selectable marker. Plant Cell Reports. 2001: 20(5): 429-436.
Privalle LS et al. Phosphomannose isomerase, a novel selectable plant selection system: mode of action and safety assessment. Proceedings of the 6th International Symposium on the Biosafety of Genetically Modified Organisms, Saskatoon, Canada. (eds. C. Fairbairn et al.) University Extension Press, Univ. Saskatchewan, Jul. 2000, pp. 171-178.
Cleasby A et al. The X-ray crystal structure of phosphomannose isomerase from *Candida albicans* at 1.7 Å resolution. Nature Structural Biology. May 1996; 3(5):470-479.
Zhang S-Z et al. Expression of the *Grifola frondosa* trehalose synthase gene and improvement of drought-tolerance in sugarcane (*Saccharum officinarum* L.). Journal of Integrative Plant Biology. 2006; 48(4): 453-459.
Elliott AR et al. *Agrobacterium*-mediated transformation of sugarcane using GFP as a screenable marker. Australian Journal of Plant Physiology. 1998; 25(6): 739-743 [Abstract Only].
Hiei Y et al. Transformation of rice mediated by *Agrobacterium tumefaciens*. Plant Molecular Biology. 1997; 35: 205-218.
Basnayake SWV et al. Embryogenic callus proliferation and regeneration conditions for genetic transformation of diverse sugarcane cultivars. Plant Cell Rep. 2011; 30: 439-448.
Chan M-T et al. Transformation of indica rice (*Oryza sativa* L.) mediated by *Agrobacterium tumefaciens*. Plant and Cell Physiology. 1992; 33(5): 577-583 Abstract.
Arencibia AD et al. An efficient protocol for sugarcane (*Saccharum* spp. L.) transformation mediated by *Agrobacterium tumefaciens*. Transgenic Research. 1998; 7: 213-222.
Pipatpanukul T et al. Transformation of indica rice (*Oryza sativa* L.) cv. RD6 mediated by *Agrobacterium tumefaciens*. Songklanakarin J Sci Technol. 2004; 26(1): 1-13.
Hiei Y et al. Efficient transformation of rice (*Oryza sativa* L.) mediated by *Agrobacterium* and sequence analysis of the boundaries of the T-DNA. The Plant Journal. 1994; 6(2) 271-282.
Dong J et al. *Agrobacterium*-mediated transformation of Javanica rice. Molecular Breeding. 1996; 2: 267-276.
Wünn J et al. Transgenic indica rice breeding line IR58 expressing a synthetic cryIA(b) gene from *Bacillus thuringiensis* provides effective insect pest control. Biotechnology. Feb. 14, 1996; 14: 171-176.
Reed J et al. Phosphomannose isomerase: an efficient selectable marker for plant transformation. In Vitro Cellular & Developmental Biology, Plant. Mar.-Apr. 2001; 37(2): 127-132.
Callis J et al. Introns increase gene expression in cultured maize cells. Genes & Development. 1987; 1: 1183-1200.
Vieira J and Messing J. The pUC plasmids, an M13mp7-derived system for insertion mutagenesis and sequencing with synthetic universal primers. Gene. 1982; 19: 259-268.
Bevan MW and Flavell RB. A chimaeric antibiotic resistance gene as a selectable marker for plant cell transformation. Nature. Jul. 14, 1983; 304:184-187.
Spencer TM et al. Bialaphos selection of stable transformants from maize cell culture. Theo Appl Genet. 1990; 79: 625-631.

(Continued)

*Primary Examiner* — David T Fox
(74) *Attorney, Agent, or Firm* — Yoshimi D. Barron

(57)    ABSTRACT

Provided herein are improved methods for transforming monocotyledonous plants, as well as an improved phosphomannose-isomerase (PMI) protein coding region and transformation vectors including the same.

11 Claims, No Drawings

(56) References Cited

OTHER PUBLICATIONS

Bourouis M and Jarry B. Vectors containing a prokaryotic dihydrofolate reductase gene transform Drosophila cells to methotrexate-resistance. EMBO J. 1983; 2(7): 1099-1104.

Braun EL and Grotewold E. Newly discovered plant c-myb-like genes rewrite the evolution of the plant myb gene family. Plant Physiology. Sep. 1999; 121: 21-24.

White J et al., A cassette containing the bar gene of *Streptomyces hygroscopicus*: a selectable marker for plant transformation. Nucl. Acids Res. 1990; 18: 1062.

Needleman SB and Wunsch CD. A general method applicable to the search for similarities in the amino acid sequence of two proteins. J Mol Biol. 1970; 48: 443-453.

Wang B et al., Expression of a modified human lysozyme gene in tobacco, J. Agricultural Biotechnology 2002, 10 (3) 237-240 [English Abstract Only].

Blochlinger K and Diggelmann H. Hygromycin B phosphotranferase as a selectable marker for DNA transfer experiments with higher eukaryotic cells. Mol Cell Biol. Dec. 1984; 4(12): 2929-2931.

\* cited by examiner

ENHANCED TRANSFORMATION OF RECALCITRANT MONOCOTS

RELATED APPLICATIONS

This application claims the benefit of U.S. Provisional Patent Application Ser. No. 61/479,131, filed Apr. 26, 2011, the disclosure of which is incorporated by reference herein in its entirety.

FIELD

The invention relates broadly to the field of plant transformation.

BACKGROUND

*Agrobacterium*-mediated gene transfer is widely used for the production of transgenic dicots. However, monocotyledonous plants (monocots) are generally less susceptible than dicots to *Agrobacterium*-mediated transformation, and thus direct DNA transfer methods such as electroporation and particle gun transformation have been more widely used. Moreover, direct DNA transfer methods suffer deficiencies, including frequent incorporation of the DNA into the host genome as multiple copies of the desired gene are rearranged together with flanking sequences from the plasmid vector. These rearrangement and integration events may result in gene expression that is aberrant and unstable in $R_0$ and progeny plants.

*Agrobacterium*-mediated gene transfer usually results in the insertion of a discrete, unrearranged DNA segment into the host genome, and thus better methods for the *Agrobacterium*-mediated transformation of monocots are needed.

SUMMARY

Provided herein are methods for increasing the transformation frequency of a monocotyledonous plant tissue, including introducing a heterologous nucleic acid comprising a coding region having one or more maize-optimized codons into a cell of the plant tissue, thereby producing a transformed cell comprising the nucleic acid; whereby the transformation frequency of the monocotyledonous plant tissue is increased as compared to a transformation frequency without maize-optimized codons in the coding region of the nucleic acid.

In some embodiments, the coding region codes for a phosphomannose-isomerase (PMI) protein.

In some embodiments, the introducing step is carried out by *Agrobacterium*-mediated transformation. In some embodiments, the monocotyledonous plant is recalcitrant to *Agrobacterium*-mediated transformation.

In some embodiments, the monocotyledonous plant tissue has a 1-, 2-, or 3-fold greater transformation frequency as compared to a transformation frequency without maize-optimized codons in the coding region of the nucleic acid.

In some embodiments, the monocotyledonous plant tissue has a transformation frequency by *Agrobacterium*-mediated transformation without maize-optimized codons of less than about 20%, 15%, 10%, or 5% as compared to a transformation frequency with maize-optimized codons in the coding region of the nucleic acid.

In some embodiments, the monocotyledonous plant tissue is maize, rice, wheat or barley tissue. In some embodiments, the monocotyledonous plant tissue is tissue of sugar cane. In some embodiments, the monocotyledonous plant tissue is an Indica variety of rice.

Further provided is a method of transforming a plant tissue (e.g., sugar cane) using a phosphomannose-isomerase (PMI) protein as a selectable marker, including: (a) introducing a heterologous nucleic acid comprising a PMI protein coding region, the PMI coding region having one or more maize-optimized codons, into a cell of the plant tissue to thereby produce a transformed cell comprising the nucleic acid, wherein the introducing step is carried out by *Agrobacterium*-mediated transformation; and, optionally, (b) regenerating a transformed plant from the transformed cell under conditions selective for PMI protein expression; to produce the transformed plant tissue.

In some embodiments, the plant tissue has a 1-, 2-, or 3-fold greater transformation frequency as compared to transformation with an expression cassette comprising a nucleic acid comprising SEQ ID NO:2.

In some embodiments, the PMI protein comprises, consists of, or consists essentially of the amino acid sequence of SEQ ID NO:3 or an amino acid sequence with 90% identity thereto. In some embodiments, the PMI protein comprises, consists of, or consists essentially of the amino acid sequence of SEQ ID NO:3 or an amino acid sequence with 95% identity thereto. In some embodiments, the coding region has 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, or 390 or more maize-optimized codons. In some embodiments, the coding region comprises, consists of, or consists essentially of at least 500, 700, or 1000 consecutive nucleotides of SEQ ID NO:2. In some embodiments, the coding region comprises, consists of, or consists essentially of a nucleic acid sequence with 90, 95, 97, 98 or 99% identity to SEQ ID NO:2. In some embodiments, the coding region has a nucleic acid sequence that hybridizes under stringent conditions to a nucleic acid of SEQ ID NO:2.

In some embodiments, the methods further include selecting a multiple shoot culture comprising the transformed cell; growing the multiple shoot culture under conditions that promote shoot elongation to produce at least one transformed shoot; and growing the at least one transformed shoot.

Also provided is a transformed multiple shoot culture produced by a method as provided herein, a plant regenerated therefrom, or a progeny thereof.

Further provided is a recombinant vector comprising a nucleic acid sequence, the nucleic acid sequence or the complement thereof comprising, consisting of, or consisting essentially of a coding region encoding: (a) the amino acid sequence of SEQ ID NO:3; or (b) an amino acid sequence having at least 90, 95, 97, 98, or 99% identity to the amino acid sequence of SEQ ID NO:3 and encoding a phosphomannose-isomerase (PMI) protein, wherein the coding region comprises one or more maize-optimized codons.

In some embodiments, the nucleic acid or nucleotide sequence may further include a Kozak sequence.

In some embodiments, the nucleotide sequence comprises at least 500, 700, or 1000 consecutive nucleotides of the nucleic acid sequence of SEQ ID NO:2. In some embodiments, the coding region comprises, consists of, or consists essentially of a nucleic acid sequence with 90, 95, 97, 98 or 99% identity to SEQ ID NO:2. In some embodiments, the coding region comprises, consists of, or consists essentially of a nucleic acid sequence that hybridizes under stringent conditions to a nucleic acid of SEQ ID NO:2.

In some embodiments, the vector may include a T-DNA border region, or may otherwise be configured or constructed for use in *Agrobacterium*-mediated transformation of plants or fungi.

Also provided is a nucleic acid sequence, the nucleic acid sequence or the complement thereof comprising a coding region encoding an amino acid sequence having at least 90% identity to the amino acid sequence of SEQ ID NO:3 and encoding a phosphomannose-isomerase (PMI) protein, wherein said coding region comprises one or more maize-optimized codons. In some embodiments, the coding region encodes the amino acid sequence of SEQ ID NO:3 or an amino acid sequence with 95% identity thereto.

BRIEF DESCRIPTION OF THE SEQUENCE LISTING

SEQ ID NO: 1 is a nucleotide sequence from *Escherichia coli* phosphomannose isomerase (PMI) gene, which corresponds to Genbank Accession No. M15380.

SEQ ID NO: 2 is a nucleotide sequence from *Zea mays* codon optimized version of the *Escherichia coli* phosphomannose isomerase (PMI) gene.

SEQ ID NO: 3 is an amino acid sequence from *Escherichia coli* phosphomannose isomerase (PMI) gene, which corresponds to EC 5.3.1.8.

SEQ ID NO: 4 is a nucleotide sequence containing a *Zea mays* Ubiquitin promoter and intron, the *Zea mays* codon optimized PMI gene and an *Agrobacterium tumefaciens* NOS terminator.

SEQ ID NO: 5 is the Kozak consensus sequence: (gcc) gccRccAUGG (SEQ ID NO: 5), where R is a purine (adenine or guanine) three bases upstream of the start codon (AUG), which is followed by another G.

DETAILED DESCRIPTION

Various embodiments of the invention are described herein. As will be appreciated by those of skill in the art, the features of the various embodiments of the invention can be combined, creating additional embodiments which are intended to be within the scope of the invention. All U.S. Patent documents cited herein are hereby incorporated by reference to the extent they are consistent with the disclosures provided herein.

As used herein, "a," "an" or "the" can mean one or more than one. For example, "an" enzyme is inclusive of a single enzyme as well as a multiplicity of enzymes. As used herein, "and/or" refers to and encompasses any and all possible combinations of one or more of the associated listed items, as well as the lack of combinations when interpreted in the alternative ("or").

As used herein, "about" means within a statistically meaningful range of a value, such as a stated concentration, time frame, weight (e.g., a percentage change (reduction or increase in weight)), volume, temperature or pH. Such a range can be within an order of magnitude, typically within 20%, more typically still within 10%, and even more typically within 5% of a given value or range. The allowable variation encompassed by "about" will depend upon the particular system under study, and can be readily appreciated by one of skill in the art.

The transitional phrase "consisting essentially of" means that the scope of a claim is to be interpreted to encompass the specified materials or steps recited in the claim "and those that do not materially affect the basic and novel characteristic(s)" of the claimed invention. Thus, the term "consisting essentially of" when used in a claim of this invention is not intended to be interpreted to be equivalent to "comprising."

"Monocotyledonous" or "monocot" plants are well known in the art, and include, but are not limited to, wheat, turf grass, maize, rice, oat, barley, sorghum, orchid, iris, lily, onion, banana, sugar cane, and palm.

"Transformation frequency" refers to the percentage of plant cells that are successfully transformed with a heterologous nucleic acid after performance of a transformation protocol on the cells to introduce the nucleic acid. In some embodiments, transformation further includes a selection protocol to select for those cells that are expressing one or more proteins encoded by a heterologous nucleic acid of interest. In some embodiments, transformation makes use of a "vector," which is a nucleic acid molecule designed for transformation into a host cell.

An increased "transformation efficiency," as used herein, refers to any improvement, such as an increase in transformation frequency and quality events that impact overall efficiency of the transformation process by reducing the amount of resources required.

"Regenerating" or "regeneration" of a plant cell is the process of growing a plant from the plant cell (e.g., plant protoplast, callus or explant).

In general, upon use of the methods taught herein, transformation frequency is increased by at least about 3%, 5%, 7%, 8%, 9%, 10%, 11%, 12%, 13%, 14%, 15%, 20%, 30%, 40%, 50%, 60%, 70%, 80%, 90% or 100% or greater, or even 1-, 2- or 3-fold or more, than the transformation frequency relative to a control. The "control" provides a reference point for measuring changes in phenotype of the subject plant or plant cell, e.g., transformation frequency/efficiency, callus quality or transformation process time. The control may include, for example, plant cells transformed with a corresponding nucleic acid without maize-optimized codons (e.g., a PMI gene).

A "recalcitrant" species, variety or cultivar as used herein is one in which the average transformation frequency using typical transformation methods is relatively low, and typically less than about 1%, 2%, 3%, 4%, 5%, 6%, 7%, 8%, 9%, 10%, 11%, 12%, 13%, 14%, 15%, 16%, 17%, 18%, 19%, 20%, 25%, or 30%. The transformation of species, varieties or cultivars recalcitrant to transformation is time consuming, laborious, and inefficient compared to the transformation of non-recalcitrant varieties, with respect to one or more methods of transformation (e.g., *Agrobacterium*-mediated transformation). Examples of species recalcitrant to *Agrobacterium*-mediated transformation include, but are not limited to, species of *Lolium* (rye grass), elite varieties of maize, species of rice (especially Indica), various turfgrass species, etc.

The term "coding region" or "coding sequence" is a nucleic acid sequence that is transcribed into mRNA, which is translated into a polypeptide when placed under the control of promoter sequences. The boundaries of the coding sequence are generally determined by the ATG start codon located at the start of the open reading frame, near the 5' end of the nucleic acid, and one or more of the TAG, TGA or TAA stop codon(s) at the end of the coding sequence, near the 3' end of the nucleic acid, and in some cases, a transcription terminator sequence located just downstream of the open reading frame at the 3' end of the nucleic acid. A nucleic acid having a coding sequence can include, but is not limited to, genomic DNA, cDNA, RNA, semisynthetic, synthetic, or recombinant nucleic acid sequences.

A "maize-optimized" or "*Zea mays* optimized" gene or coding region is a gene or coding region where one or more of the codons encoding the protein of interest (by way of example, in some embodiments 10, 20, 30, 40, 50, 60, 70, 80, 90, 95, 99, or even 100% of the native codons) have been changed from the native nucleic acid sequence to a nucleic acid sequence that is optimized with respect to maize. See Koziel et al., U.S. Pat. No. 6,075,185, which is incorporated by reference herein in its entirety. Specifically, the following "maize-optimized" codons may be used: Ala, GCC; Arg, CGC; Asn, AAC; Asp, GAC; Cys, TGC; Gln, CAG; Glu, GAG; Gly, GGC; His, CAC; Ilc, ATC; Leu, CTG; Lys, AAG; Met, ATG; Phe, TTC; Pro, CCC; Ser, AGC; Thr, ACC; Trp, TGG; Tyr, TAC; and Val, GTG.

Also contemplated are nucleic acid sequences that are at least substantially identical to a nucleic acid sequence as provided herein. This may include nucleic acid sequences that hybridize under low, medium, high or very high stringency conditions to the original nucleic acid sequence. Also contemplated is the alternative use of fragments or variants (e.g., a substantially identical variant) of any of the polypeptides described herein. Two nucleotide sequences are "substantially identical" or share "substantial identity" if the nucleotide sequences are at least about 70%, 75%, 80%, 85%, 90%, 95%, 97%, 98%, 99% or more identical.

As is known in the art, a number of different mathematical algorithms and programs can be used to determine the degree of sequence identity between two nucleotide sequences. For example, the percent identity between two nucleotide sequences can be determined using the Needleman and Wunsch (1970) J. Mol. Biol. 48:444-453 algorithm that has been incorporated into the GAP program in the GCG software package, using either a Blossum 62 matrix or a PAM250 matrix.

Exemplary "hybridization" conditions are provided herein. Guidance for performing hybridization reactions can be found in Current Protocols in Molecular Biology (1989) John Wiley & Sons, N.Y., 6.3.1-6.3.6. Aqueous and non-aqueous methods are described in that reference, and either can be used. For example, "low stringency" hybridization conditions can comprise hybridization in 6× sodium chloride/sodium citrate (SSC) at about 45° C., followed by two washes in 0.5×SSC, 0.1% SDS, at least at 50° C. An illustration of "medium stringency" hybridization conditions are hybridization in 6×SSC at about 45° C., followed by one or more washes in 0.2×SSC, 0.1% SDS at 55° C. One example of "stringent" hybridization conditions comprise hybridization at 65° C. and washing three times for 15 minutes with 0.25× SSC, 0.1% SDS at 65° C. Additional exemplary stringent hybridization conditions comprise hybridization in 0.02 M to 0.15 M NaCl at temperatures of about 50° C. to 70° C. or 0.5×SSC 0.25% SDS at 65° C. for 15 minutes, followed by a wash at 65° C. for a half hour or hybridization at 65° C. for 14 hours followed by 3 washings with 0.5×SSC, 1% SDS at 65° C. Other exemplary highly selective or stringent hybridization conditions comprise 0.02 M to 0.15 M NaCl at temperatures of about 50° C. to 70° C. or 0.5×SSC 0.25% SDS at 65° C. for 12-15 hours, followed by three washes at 65° C. for 15-90 minutes each. Probe hybridization can be scored visually to determine a binary (positive versus negative) value, or the probes can be assigned a score based on the relative strength of their hybridization on a 10-point scale.

An "isolated polynucleotide" or "isolated nucleic acid" (and similar terms) can refer to a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term "isolated" can also refer to a polynucleotide or nucleic acid that is substantially free of cellular material, viral material, and/or culture medium (e.g., when produced by recombinant DNA techniques), or chemical precursors or other chemicals (e.g., when chemically synthesized). "Isolated" does not necessarily mean that the preparation is technically pure (homogeneous), but it is sufficiently pure to provide the polynucleotide or nucleic acid in a form in which it can be used for the intended purpose. In certain embodiments, the isolated polynucleotide or nucleic acid is at least about 50% pure, e.g., at least about 60%, 70%, 80%, 90%, 95%, 96%, 97%, 98%, or 99% or more pure (e.g., with respect to other cellular material as compared to its natural state in a cell).

Similarly, an "isolated" cell or protein refers to a cell or protein that is at least partially separated from other components with which it is normally associated in its natural state. For example, an isolated cell can be a cell in culture medium.

The terms "heterologous" and "exogenous" when used herein to refer to a nucleic acid sequence (e.g., a DNA or RNA sequence), is a sequence that originates from a source foreign to the particular host cell, or, if from the same source, is modified from its original form. The terms "heterologous" and "exogenous" also include non-naturally occurring multiple copies of a naturally occurring DNA sequence. Thus, the terms refer to a nucleic acid segment that is foreign to the cell.

Unless the context indicates otherwise, the term "gene" is not intended to be limited to a nucleic acid as it exists in its native state in the genome of an organism or virus, e.g., including the native introns and regulatory sequences such as promoter, initiation and termination sequences. Thus, unless indicated otherwise by context, as used herein the term "gene" is construed more broadly as a nucleic acid encoding a protein or functional, untranslated RNA.

Fragments of the nucleic acid sequences provided herein are also contemplated, e.g., comprising, consisting of, or consisting essentially of at least 100, 150, 200, 250, 300, 350, 400, 450, 500, 550, 600, 650, 700, 750, 800, 850, 900, 950, 1000, etc., consecutive nucleotides of the sequence.

Functional fragments of an encoded protein of interest are also included. For example, the manA gene encoding a phosphomannose isomerase enzyme (PMI), which is useful as a selectable marker, allows a plant to utilize mannose as a carbon source. PMI is an enzyme that breaks down mannose-6-phosphate to fructose-6-phosphate, which allows a plant transfected with a nucleic acid encoding PMI to use mannose as a sugar source. A functional fragment of the PMI protein is a fragment that still performs this function of breaking down rnannoe-6-phosphate to fructose-6-phosphate. The structure of the PMI protein is known, and thus a functional fragment of the same should be apparent to one of skill in the art. See, e.g., Cleasby et al., "The X-ray crystal structure of phosphomannose isomerase from *Candida albicans* at 1.7 Å resolution," Nature Structural Biology 3:470-479 (1996).

"Expression" of a nucleic acid as used herein refers to the transcription, and optionally, translation of a gene or other nucleic acid encoding a protein or polypeptide.

The nucleic acid sequences may be present in nucleic acid constructs such as expression cassettes. "Expression cassette" as used herein means a nucleic acid molecule capable of directing expression of a particular nucleotide sequence in an appropriate host cell, generally comprising a promoter operatively linked to a nucleotide sequence of interest (e.g., a nucleotide sequence encoding a protein or polypeptide of interest). It may also include sequences required for proper translation of the nucleotide sequence. In some embodiments, the expression cassette will comprise a selectable marker gene for the selection of transformed cells. Selectable marker genes are utilized for the selection of transformed cells or tissues. In some embodiments, the expression cassette is between 500 bp and 30,000 bp, or between 1000 bp and 20,000 bp, or between 5,000 and 15,000 bp in size.

In some embodiments, an expression cassette is provided which comprises the selectable marker gene PMI. In some embodiments, the PMI gene has a coding region comprising one or more maize-optimized PMI codons. The expression cassette may also include a heterologous nucleic acid of interest (e.g., one that encodes a protein of interest) and/or a plurality of restriction sites for insertion of a heterologous nucleic acid of interest (e.g., a multiple cloning site), as known in the art.

The expression of the nucleotide sequence in the expression cassette may be under the control of a constitutive promoter or of an inducible promoter that initiates transcription primarily when the host cell is exposed to some particular external stimulus. The promoter can optionally be specific or show a preferential expression for a particular tissue or organ or stage of development.

Any promoter capable of driving expression in the plant of interest may be used in the practice of the invention. The promoter may be native or analogous, or foreign or heterologous, to the plant host. The choice of promoters to be included depends upon several factors, including, but not limited to, efficiency, selectability, inducibility, desired expression level, and cell- or tissue-preferential expression. In some embodiments, the promoter is a monocot promoter (e.g., a maize Ubiquitin) promoter, rice Ubiquitin or rice Actin 1 promoter). It is a routine matter for one of skill in the art to modulate the expression of a sequence by appropriately selecting and positioning promoters and other regulatory regions relative to that sequence.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183-1200 (1987)). In the same experimental system, the intron from the maize bronze 1 gene had a similar effect in enhancing expression. Intron sequences have been routinely incorporated into plant transformation vectors, typically within the non-translated leader.

A leader sequence such as a Kozak sequence may also be added. The Kozak sequence has the consensus (gcc)gccRccAUGG, where R is a purine (adenine or guanine) three bases upstream of the start codon (AUG), which is followed by another G (SEQ ID NO: 5).

In addition, a transcription terminator may be used. A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. An additional terminator may be added to the native transcription terminator, if desired.

The expression constructs described herein can be introduced into the plant cell (i.e., the plant cell being "transformed") in a number of art-recognized ways. In the context of a polynucleotide, for example, a nucleotide construct of interest is presented to the plant in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, and/or as part of a breeding protocol. Methods for introducing polynucleotides into plants are known in the art, including, but not limited to, transient transformation methods and stable transformation methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant, the introduced polynucleotide is stably incorporated into the plant genome (nuclear or plastid), or otherwise stably incorporated among the plant's genetic material (e.g., a stable episome). In representative methods, "stable transformation" or "stably transformed" is intended to mean that a polynucleotide, for example, a nucleotide construct described herein, introduced into a plant integrates into the genome of the plant and is capable of being inherited by the progeny thereof in one or more generations.

Numerous transformation vectors available for plant transformation are known to those of ordinary skill in the plant transformation arts. The selection of vector will depend upon the preferred transformation technique and the target species for transformation. For certain target species, different antibiotic or herbicide selection markers may be used. Selection markers used routinely in transformation include the nptII gene, which confers resistance to kanamycin and related antibiotics (Messing & Vierra. Gene 19: 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet. 79: 625-631 (1990)), the hph gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), and the EPSPS gene, which confers resistance to glyphosate (U.S. Pat. Nos. 4,940,935 and 5,188,642).

Selectable markers also include the gene encoding phosphomannose-isomerase (PMI), which provides the ability to metabolize mannose (U.S. Pat. Nos. 5,767,378 and 5,994,629, which are incorporated by reference herein). A plant cell transformed with a PMI gene may be selected by growing on media containing mannose only or mannose plus sucrose.

In traditional transformation protocols, plant cells are placed on culture media containing salts, hormones and a carbon source, usually sucrose. For the PMI/mannose selection system, plant tissues may be cultured on a similar medium supplemented with either mannose as the unique source of carbon or with media containing both sucrose and mannose. While mannose has no direct adverse effect on plant cells, the subsequent selection is considered to be a consequence of its phosphorylation to mannose 6-phosphate by hexokinase. In the absence of PMI, the mannose 6-phosphate accumulates, and the cells stop growing. Stein & Hansen (1999) reported that mannose 6-phosphate, itself, induces apoptosis (Plant Physiology 121: 1-9). The authors had identified a mannose 6-phosphate induced nuclease that is responsible for the development of the laddering of DNA, a characteristic of apoptosis.

In some embodiments, bacteria from the genus *Agrobacterium* can be utilized to transform plant cells. See, e.g., U.S. Pat. No. 6,037,522 to Dong et al. Generally, plant cells are transformed using *Agrobacterium*, and the transformed cells are regenerated into transgenic plants. *Agrobacterium*-mediated transformation of plant cells include the use of bacterial strain(s) classified among the Rhizobiaceae, including *Agrobacterium* sp., *Rhizobium* sp., and *Sinorhizobium* sp., among others. Depending upon the plant species, the transformed cells may be derived from leaves, roots, hypocotyls, petioles, cotyledons, or seeds. Vectors useful for *Agrobacterium*-mediated transformation may include border sequences, as known in the art. "Border sequence," e.g., right border (RB) or left border (LB), refers to a directly repeated nucleic acid sequence defining an end of the transferred DNA (T-DNA) region, typically about 24 bp in length. Border sequences may be from a Ti or Ri plasmid of *Agrobacterium* sp., or may be plant derived sequences that function similarly. "T-DNA Border region" refers to the RB or LB sequence and associated flanking sequence, typically about 100 bp in length, and may include a transformation enhancer sequence, if desired.

For example, rice (*Oryza sativa*) can be used for generating transgenic plants. Various rice cultivars can be used (Hiei et al., 1994, Plant Journal 6:271-282; Dong et al., 1996, Molecular Breeding 2:267-276; Hiei et al., 1997, Plant Molecular Biology, 35:205-218). An exemplary protocol is provided below. However, those skilled in the art will appreciate that the various media constituents described therein may be either varied in quantity or substituted. As an exemplary protocol, embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about 2 days at 28° C. *Agrobacterium* is re-suspended in liquid MS-CIM medium. The *Agrobacterium* culture is diluted to an $OD_{600}$ of 0.2-0.3 and acetosyringone is added to a final concentration of 200 µM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., In Vitro Cell. Dev. Biol.-Plant 37:127-132), cultures may be transferred to selection medium containing mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse ($T_0$ generation), grown to maturity, and the $T_1$ seed is harvested.

In some embodiments, indica rice (*Oryza sativa* L. ssp. indica) can be used for generating transgenic plants. Various indica rice cultivars can be used (Thodsaporn Pipatpanukul et al., Songklanakarin J. Sci. Technol., (26)1, 7, 1-13 (2004); Joachim Wtinn et al., Nature Biotechnology 14, 171-176 (1996); Ming-Tsair Chan et al. Plant Cell Physiol, 33(5): 577-583 (1992)). Those skilled in the art will appreciate that the various media constituents described below may be either varied in quantity or substituted. In an exemplary protocol, embryogenic responses are initiated and/or cultures are established from mature seed by culturing on Callus Induction Medium (CIM medium) (MS basal salts, 4.3 g/liter; B5 vitamins (200×), 5 ml/liter; Sucrose, 20 g/liter; 2,4-D (1 mg/ml), 2 ml/liter; adjust pH to 5.8 with 1 N KOH; Phytagel, 7 gaiter. Initial stages of culture response or established culture lines are inoculated and co-cultivated with, e.g., the *Agrobacterium tumefaciens* strain EHA101 (*Agrobacterium*) containing the desired vector construction. *Agrobacterium* may be cultured from glycerol stocks on solid YPC medium (100 mg/L spectinomycin and any other appropriate antibiotic) for about two days at 28° C., and re-suspended in liquid MS-D2 medium. The *Agrobacterium* culture is diluted to an $OD_{600}$ of 0.2-0.3 and acetosyringone is added to a final concentration of 400 µM. Acetosyringone is added before mixing the solution with the sugar cane cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days in the dark. The cultures are then transferred to MS-D2 medium with Ticarcillin (400 mg/liter) to inhibit the growth of *Agrobacterium*. For constructs utilizing the PMI selectable marker gene (Reed et al., In Vitro Cell. Dev. Biol.-Plant 37:127-132) (e.g., the *Zea mays* optimized PMI gene), cultures may be transferred to selection medium containing Mannose as a carbohydrate source (MS with 1% Mannose, 400 mg/liter Ticarcillin), and cultured for 3-4 weeks in the dark. Resistant colonies are then transferred to regeneration induction medium (MS with no 2,4-D, 2 mg/L IAA, Zeatin, 200 mg/liter Ticarcillin, 1% Mannose and Phytagel, 2 g/liter) and grown in the dark for 14 days, and then moved to the light growth room for 14 days. Regenerated shoots with roots are transferred to GA-7's with maintenance medium (MS with no hormones and 2% sucrose, 200 mg/liter Ticarcillin) for 3-4 weeks and then moved to the greenhouse when they are large enough. Plants are transplanted to soil in the greenhouse ($T_o$ generation), and grown to maturity.

As another example, sugar cane (*Saccharum*) can be used for generating transgenic plants. Various sugar cane cultivars can be used (Ariel D. Arencibia et al., Transgenic Research 7, 213-222 (1998); Adrian Elliott et al., Aust. J. Plant Physiol. 25, 739-743 (1998); Z Wang, et al., J. Agricultural Biotechnology 2002, 10 (3) 237-240; S Zhang et al., J. Integrative Plant Biology 2006, 48(4):453-459; Basanayake et al., Plant Cell Report 2011, 30: 439-448). Those skilled in the art will appreciate that the various media constituents described below may be either varied in quantity or substituted. In an exemplary protocol, embryogenic responses are initiated and/or cultures are established from sugar cane young leaves by culturing on SC-D2 medium (MS basal salts, 4.3 g/liter; B5 vitamins (200×), 5 ml/liter; Sucrose, 30 g/liter; 2,4-D (1 mg/ml), 2 ml/liter; adjust pH to 5.8 with 1 N KOH; Phytablend, 7 g/liter. Either mature embryos at the initial stages of culture response or established culture lines are inoculated and co-cultivated with the *Agrobacterium tumefaciens* strain EHA101 (*Agrobacterium*) containing the desired vector construction. *Agrobacterium* is cultured from glycerol stocks on solid YPC medium (100 mg/L spectinomycin and any other appropriate antibiotic) for about two days at 28° C. *Agrobacterium* is re-suspended in liquid MS-D2 medium. The *Agrobacterium* culture is diluted to an $OD_{600}$ of 0.3-0.4 and acetosyringone is added to a final concentration of 400 µM. Acetosyringone is added before mixing the solution with the sugar cane cultures to induce *Agrobacterium* for DNA transfer to the plant cells. For inoculation, the plant cultures are immersed in the bacterial suspension. The liquid bacterial suspension is removed and the inoculated cultures are placed on empty plate for co-cultivation and incubated at 22° C. for two days. The cultures are then transferred to SC-D2 medium with Ticarcillin (400 mg/liter) to inhibit the growth of *Agrobacterium*. For constructs utilizing the PMI selectable marker gene (Reed et al., In Vitro Cell. Dev. Biol.-Plant 37:127-132) (e.g., the *Zea mays* optimized PMI gene), cultures may be transferred to selection medium containing mannose as a carbohydrate source (MS with 0.8% Mannose, 400 mg/liter Ticarcillin), and cultured for 3-4 weeks in the dark. Resistant colonies are then transferred to regeneration induction medium (MS with no 2,4-D, 2 mg/L BAP, 200 mg/liter Ticarcillin, 0.6% Mannose) and grown in the dark for 7 days, and then moved to the light growth room for 14 days. Regenerated shoots are transferred to SC-Root-M6-T medium (MS with no hormones and 0.6% mannose, 200 mg/liter Ticarcillin) for 3-4 weeks and then moved to the greenhouse when they are large enough and have adequate roots. Plants are transplanted to soil in the greenhouse (To generation), and grown to maturity.

See also PCT Patent Publication No. WO/2010/151634 to De Lucca et al., which is incorporated by reference herein.

A nucleotide sequence(s) of interest in the expression cassette can be any nucleotide sequence(s) of interest and can be obtained from prokaryotes or eukaryotes (e.g., bacteria, fungi, yeast, viruses, plants, mammals) or the nucleotide sequence of interest can be synthesized in whole or in part. Further, the nucleotide sequence of interest can encode a polypeptide of interest or can be transcribed to produce a functional RNA. In particular embodiments, the functional RNA can be expressed to improve an agronomic trait in the plant (e.g., tolerance to drought, heat stress, high temperature, salt, or resistance to herbicides disease, insects or other pests [e.g., a *Bacillus thuringiensis* endotoxin], and the like), to confer male sterility, to improve fertility and/or enhance nutritional quality (e.g., enzymes that enhance nutritional quality). A polypeptide of interest can be any polypeptide encoded by a nucleotide sequence of interest. The nucleotide sequence may further be used in the sense orientation to achieve suppression of endogenous plant genes, as is known by those skilled in the art (see, e.g., U.S. Pat. Nos. 5,283,184; 5,034,323).

The nucleotide sequence of interest can encode a polypeptide that imparts a desirable agronomic trait to the plant (as described above), confers male sterility, improves fertility and/or improves nutritional quality. Other suitable polypeptides include enzymes that can degrade organic pollutants or remove heavy metals. Such plants, and the enzymes that can be isolated therefrom, are useful in methods of environmental protection and remediation. Alternatively, the heterologous nucleotide sequence can encode a therapeutically or pharmaceutically useful polypeptide or an industrial polypeptide (e.g., an industrial enzyme). Therapeutic polypeptides include, but are not limited to, antibodies and antibody fragments, cytokines, hormones, growth factors, receptors, enzymes and the like.

Additional non-limiting examples of polypeptides of interest that are suitable for use with this invention (e.g., to be expressed in a developmental stage-specific or tissue specific manner) include polypeptides associated with nutrient uptake including transport and assimilation of organic and inorganic nutrients. Thus, for example, polypeptides involved in nitrogen transport and assimilation, including, but not limited to, nitrite transporter (NiTR1 gene), high affinity nitrate transporter, nitrate and chloride transporter, nitrate reductase, NADH-dependent nitrate reductase, oligopeptide and nitrate transporter, ammonium transporter (Osamt1.1; 1.3; 2.2; 3.1; 5.1), nitrate transporter (Atnrtl 1), symbiotic ammonium transporter, ammonium transporter, NADH-dependent glutamate synthase, nitrate transporter, ammonium transporter (Osamt1.1; 5.2), high affinity nitrate transporter (nar2.1), gln4, gl5, nitrate transporter (nrt1.1), amino acid transport protein, NADH-dependent nitrate reductase (nr1, nia1), nitrate transporter (nrt1-5), ammonium transporter (Osamt2.1; 2.3; 3.3), high affinity nitrate transporter (nar2.1; nar2.2), nitrate transporter (*Glycine max* nrt1.2), ferredoxin-dependent glutamate synthase, high affinity nitrate transporter (nrt2.1)

Other non-limiting examples of polypeptides of interest include those involved in resistance to insects, nematodes and pathogenic diseases. Such polypeptides can include, but are not limited to, glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, a-amylase inhibitor or protease inhibitors (cowpea trypsin inhibitor), lectins such as wheatgerm agglutinin, RNAses or ribozymes. Further non-limiting examples include nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents of these, chitinases, for example from beans (Brogue et al. (1991) Science 254:1194-1197), "polygalacturonase-inhibiting protein" (PGIP), thaumatine, invertase and antimicrobial peptides such as lactoferrin (Lee T J et al. (2002) *J Amer Soc Horticult Sci* 127(2):158-164) (See, e.g., U.S. Pat. No. 8,071, 749) as well as the plant defense genes, including but not limited to, PR1, BG2, PR5, and NPR1 (or NIM1).

Also useful with the present invention are nucleotide sequences encoding polypeptides involved in plant hormone production or signaling, including, but not limited to, auxins, cytokinins, gibberellins, strigolactones, ethylene, jasmonic acid, and brassinosteroids, as well as other nucleotide and polypeptide sequences that regulate or effect root and leaf growth and development. Non-limiting examples of such nucleotide and/or polypeptide sequences include GA-Deficient-1 (GA1; CPS), Gibberellin 20-Oxidase (GA20ox, GA5 (in At)), Gibberellin 2-beta-dioxygenase (GA2ox), Gibberellin 3-Oxidase (GA3ox), GA-Insensitive (GAI), GA Regulated MYB(GAMYB), GCA2 Growth Controlled By ABA 2 (GCA2), G-Protein Coupled Receptor (GCR1), Glycosyl Hydrolase Family-45 (GH45), tryptophan synthase alpha chain (e.g., GRMZM2G046163, GRMZM2G015892), Auxin Binding Protein 1 (ABP1), IAA-amino acid hydrolase ILR1 (e.g., GRMZM2G091540), phosphoribosylanthranilate transferase, Indole Acetic Acid 17/Auxin Resistant 3(IAA17, AXR3), Indole Acetic Acid 3/Short Hypocotyl (IAA3, SHY2), IAA-lysine synthetase (iaaL), tryptophan monooxygenase (iaaM), IAA-Aspartic Acid Hydrolase (IaaspH), IAA-Glucose Synthase (IAGLU) IndoleAcetamide Hydrolase (IAH), Indole-3-Acetaldehyde Oxidase (IAO), IAA-ModifiedProtein (IAP1), Auxin Response factors (ARFs), small auxin up RNA (SAUR), Induced By Cytokinin 6 (Same as ARR5) (IBC6), Induced By Cytokinin 7 (Same as ARR4) IBC7, Viviparous-14 (PPM, $PLA_2$ (Zhu J-K. *Annual Review of Plant Biology* 2002, 53(1):247-273), ATPLC2 (Benschop et al. *Plant Physiology* 2007, 143(2):1013-1023), inositol polyphosphate 5-phosphatase (AtSPTaseI), calcium-dependent protein kinases (CDPKs), calcineurin B-like (CBL) calcium sensor protein CBL4/SOS3, CIPK-like protein 1, ACC (1-aminocyclopropane-1-carboxylate) synthase, ACC oxidase, phosphatase 2C ABI1, TINY, maize lipoxygenase 7 (GRMZM2G070092), allene oxide synthase (AOS) (e.g., GRMZM2G033098 and GRMZM2G376661), short chain alcohol dehydrogenases (ADH), Tasselseed2 (Ts2), Tasselseed1 (Ts1), Supercentipedel (Scn1/GDI1, e.g., AT2G44100), RDH2 (Carol et al. *Nature* 2005, 438(7070): 1013-1016.), G-signaling proteins, *Morphogenesis of Root Hair* (*MRH*), AtAGC2-1 (e.g., At3g25250), Cellulose Synthase-Like D3 (CSLD3), xylosyltransferase 2 (e.g., At4g02500, AtXX2), xyloglucan endotransglucosylase/hydrolase 26 (e.g., AtXTH26, At4g28850), xyloglucan endotransglycosylase, xyloglucan galactosyltransferase (MUR3 (e.g., AT2G20370), ARP2/3 (WURM/DISTORTED 1) complex, and germin-like protein (e.g., AT5G39110).

Other nucleotide sequences and polypeptides that are suitable for use with the present invention include those that confer the "stay-green" phenotype (See, Hortensteiner, S. *Trends in Plant Science* 14: 155-162 (2009)). Non-limiting examples of such nucleotide sequences include MtSGR, MsSGR (Zhou et al. *Plant Physiol,* 157: 1483-1496 (2011)), STAY-GREEN (SGR or SGN) (Jiang et al., *Plant J* 52: 197-209 (2007)), Park et al., *Plant Cell* 19: 1649-1664 (2007)), NONYELLOWING (NYE1) (Ren et al., *Plant Physiol* 144: 1429-1441 (2007)), and/or GREEN-FLESH (GF) or CHLOROPHYLL RETAINER(CL) (Barry et al., *Plant Physiol* 147: 179-187 (2008)).

Polynucleotides involved in grain filling are also useful with the present invention and include, but are not limited to GIF1 (GRAIN INCOMPLETE FILLING 1) from rice.

Other non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903; 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/.

Nucleotide sequences conferring resistance/tolerance to an herbicide that inhibits the growing point or meristem, such as an imidazalinone or a sulfonylurea can also be suitable in some embodiments of the invention. Exemplary nucleotide sequences in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

In embodiments of the invention, the nucleotide sequence increases tolerance of a plant, plant part and/or plant cell to heat stress and/or high temperature. The nucleotide sequence can encode a polypeptide or inhibitory polynucleotide (e.g., functional RNA) that results in increased tolerance to heat stress and/or high temperature. Suitable polypeptides include without limitation water stress polypeptides, ABA receptors, and dehydration proteins (e.g., dehydrins (ERDs)).

In representative embodiments, nucleotide sequences that encode polypeptides that provide tolerance to water stress (e.g., drought) are used. Non-limiting examples of polypeptides that provide tolerance to water stress include: water channel proteins involved in the movement of water through membranes; enzymes required for the biosynthesis of various osmoprotectants (e.g., sugars, proline, and Glycine-betaine); proteins that protect macromolecules and membranes (e.g., LEA protein, osmotin, antifreeze protein, chaperone and mRNA binding proteins); proteases for protein turnover (thio)proteases, Clp protease and ubiquitin); and detoxification enzymes (e.g., glutathione S-transferase, soluble epoxide hydrolase, catalase, superoxide dismutase and ascorbate peroxidase). Non-limiting examples of proteins involved in the regulation of signal transduction and gene expression in response to water stress include protein kinases (MAPK, MAPKKK, S6K, CDPK, two-component H is kinase, Bacterial-type sensory kinase and SNF1); transcription factors (e.g., MYC and bZIP); phospholipase C; and 14-3-3 proteins.

Nucleotide sequences that encode receptors/binding proteins for abscisic acid (ABA) are also useful in the practice of the present invention. Non-limiting examples of ABA binding proteins/receptors include: the Mg-chelatase H subunit; RNA-binding protein FCA; G-protein coupled receptor GCR2; PYR1; PYL5; protein phosphatases 2C ABI1 and ABI2; and proteins of the RCAR (Regulatory Component of the ABA Receptor) family.

In embodiments of the invention, the nucleotide sequence of interest encodes a dehydration protein, also known as a dehydrin (e.g., an ERD). Dehyration proteins are a group of proteins known to accumulate in plants in response to dehydration. Examples include WCOR410 from wheat; PCA60 from peach; DHN3 from sessile oak, COR47 from *Arabidopsis thaliana*; Hsp90, BN59, BN115 and Bnerd10 from *Brassica napes*; COR39 and WCS19 from *Triticum aestivum* (bread wheat); and COR25 from *Brassica rapa* subsp. *Pekinensis*. Other examples of dehydration proteins are ERD proteins, which include without limitation, ERD1, ERD2, ERD4, ERD5, ERD6, ERD8, ERD10, ERD11, ERD13, ERD15 and ERD16.

Polypeptides encoded by nucleotide sequences conferring resistance to glyphosate are also suitable for use with the present invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene. Heterologous nucleotide sequences suitable to confer tolerance to the herbicide glyphosate also include, but are not limited to the *Agrobacterium* strain CP4 glyphosate resistant EPSPS gene (aroA:CP4) as described in U.S. Pat. No. 5,633,435 or the glyphosate oxidoreductase gene (GOX) as described in U.S. Pat. No. 5,463,175. Other heterologous nucleotide sequences include genes conferring resistance to herbicides that act to inhibit the action of acetolactate synthase (ALS), in particular the sulfonylurea-type herbicides (e.g., mutant forms of the acetolactate synthase (ALS) gene that lead to such resistance, in particular the S4 and/or Hra mutations), genes coding for resistance to herbicides that act to inhibit the action of glutamine synthase, such as phosphinothricin or basta (e.g., the bar gene). The bar gene encodes resistance to the herbicide basta, the nptII gene encodes resistance to the antibiotics kanamycin and geneticin, and the ALS gene encodes resistance to the herbicide chlorsulfuron.

Nucleotide sequences coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable nucleotide sequences of interest include those coding for resistance to herbicides that inhibit photosynthesis, such as a triazine and a benzonitrile (nitrilase). See, U.S. Pat. No. 4,810,648. Additional suitable nucleotide sequences coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are nucleotide sequences conferring resistance to a protox enzyme, or that provide enhanced resistance to plant diseases; enhanced tolerance of adverse environmental conditions (abiotic stresses) including but not limited to drought, heat stress, high temperature, cold, excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Insecticidal proteins useful in the invention may be produced in an amount sufficient to control insect pests, i.e., insect controlling amounts. It is recognized that the amount of production of insecticidal protein in a plant useful to control insects may vary depending upon the cultivar, type of insect, environmental factors and the like. Suitable heterologous nucleotide sequences that confer insect tolerance include those which provide resistance to pests such as rootworm, cutworm, European Corn Borer, and the like. Exemplary nucleotide sequences include, but are not limited to, those that encode toxins identified in *Bacillus* organisms (see, e.g., WO 99/31248; U.S. Pat. Nos. 5,689,052; 5,500,365; 5,880,275); *Bacillus* thuringiensis toxic protein genes (see, e.g., U.S. Pat. Nos. 5,366,892; 5,747,450; 5,737,514; 5,723,756; 5,593,881; 6,555,655; 6,541,448; 6,538,109; Geiser, et al. (1986) Gene 48:109); and lectins (Van Damme et al. (1994) Plant Mol. Biol. 24:825). Nucleotide sequences encoding *Bacillus thuringiensis* (Bt) toxins from several subspecies have been cloned and recombinant clones have been found to be toxic to lepidopteran, dipteran and coleopteran insect larvae (for example, various delta-endotoxin genes such as Cry1Aa, Cry1Ab, Cry1Ac, Cry1B, Cry1C, Cry1D, Cry1Ea, Cry1Fa, Cry3A, Cry9A, Cry9C and Cry9B; as well as genes encoding vegetative insecticidal proteins such as Vip1, Vip2 and Vip3). A full list of Bt toxins can be found on the worldwide web at *Bacillus thuringiensis* Toxin Nomenclature Database maintained by the University of Sussex (see also, Crickrnore et al. (1998) *Microbiol. Mol. Biol. Rev.* 62:807-813).

Polypeptides that are suitable for production in plants further include those that improve or otherwise facilitate the conversion of harvested plants and/or plant parts into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content and/or increased vitamin content.

Polypeptides of interest also include, for example, those resulting in, or contributing to, a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In one embodiment, the polypeptide of interest contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced by xylanases. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In another embodiment, a polypeptide useful for the present invention can be a polysaccharide degrading enzyme. Plants producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme or other glucoamylases.

Polysaccharide-degrading enzymes include: starch degrading enzymes such as alpha-amylases (EC 3.2.1.1), glucuronidases (E.C. 3.2.1.131), exo-1,4-alpha-D glucanases such as amyloglucosidases and glucoamylase (EC 3.2.1.3), beta-amylases (EC 3.2.1.2), alpha-glucosidases (EC 3.2.1.20), and other exo-amylases, starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-beta-D-glucanase (EC 3.2.1.39), beta-glucosidase (EC 3.2.1.21); c) L-arabinases, such as endo-1,5-alpha-L-arabinase (EC 3.2.1.99), alpha-arabinosidases (EC 3.2.1.55) and the like; d) galactanases such as endo-1,4-beta-D-galactanase (EC 3.2.1.89), endo-1,3-beta-D-galactanase (EC 3.2.1.90), alpha-galactosidase (EC 3.2.1.22), beta-galactosidase (EC 3.2.1.23) and the like; e) mannanases, such as endo-1,4-beta-D-mannanase (EC 3.2.1.78), beta-mannosidase (EC 3.2.1.25), alpha-mannosidase (EC 3.2.1.24) and the like; f) xylanases, such as endo-1,4-beta-xylanase (EC 3.2.1.8), beta-D-xylosidase (EC 3.2.1.37), 1,3-beta-D-xylanase, and the like; and g) other enzymes such as alpha-L-fucosidase (EC 3.2.1.51), alpha-L-rhamnosidase (EC 3.2.1.40), levanase (EC 3.2.1.65), inulanase (EC 3.2.1.7), and the like.

Further enzymes which may be used with the present invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*.

Other useful enzymes include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); cellobiohydrolases; esterases such as ferulic acid esterase (EC 3.1.1.73) and acetyl xylan esterases (EC 3.1.1.72); and cutinases (e.g. E.C. 3.1.1.74).

The nucleotide sequence can encode a reporter polypeptide (e.g., an enzyme), including but not limited to Green Fluorescent Protein, β-galactosidase, luciferase, alkaline phosphatase, the GUS gene encoding β-glucuronidase, and chloramphenicol acetyltransferase.

Where appropriate, the nucleotide sequence of interest may also be optimized for increased expression in a transformed plant, e.g., by using plant preferred codons. Methods for synthetic optimization of nucleic acid sequences are available in the art. The nucleotide sequence of interest can be optimized for expression in a particular host plant or alternatively can be modified for optimal expression in monocots. See, e.g., EP 0 359 472, EP 0 385 962, WO 91/16432; Perlak et al., *Proc. Natl. Acad. Sci. USA* 88, 3324 (1991), and Murray et al., *Nuc. Acids Res.* 17, 477 (1989), and the like. Plant preferred codons can be determined from the codons of highest frequency in the proteins expressed in that plant.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Some aspects of the present invention are exemplified in greater detail in the examples provided below.

EXAMPLES

Example 1

Conversion of PMI Gene

Mannose-6-phosphate isomerase (PMI) protein encoded by the *E. coli* manA gene, described in Negrotto et al. *Plant Cell Reports* 19: 798-803 (2000) (coding sequence provided below as SEQ ID NO:1), was modified by incorporating maize preferred codons.

```
E. coli PMI (1176bp)
                                           (SEQ ID NO: 1)
atgcaaaaactcattaactcagtgcaaaactatgcctggggcagcaaaa cggcgttgactgaactttatggtatggaaatccgtccagccagccgat ggccgagctgtggatgggcgcacatccgaaaagcagttcacgagtgcag aatgccgccggagatatcgtttcactgcgtgatgtgattgagagtgata aatcgactctgctcggagaggccgttgccaaacgctttggcgaactgcc tttcctgttcaaagtattatgcgcagcacagccactctccattcaggtt catccaaacaaacacaattctgaaatcggttttgccaaagaaatgccg caggtatcccgatggatgccgccgagcgtaactataaagatcctaacca caagccggagctggttttttgcgctgacgcctttccttgcgatgaacgcg tttcgtgaatatccgagattgtctccctactccagccggtcgcaggtgc acatccggcgattgctcacttttacaacagcctgatgccgaacgttta agcgaactgttcgccagcctgttgaatatgcagggtgaagaaaaatccc gcgcgctggcgattttaaaatcggccctcgatagccagcagggtgaacc gtggcaaacgattcgtttaatttctgaattttacccggaagacagcggt ctgttctcccgctattgctgaatgtggtgaaattgaaccctggcgaag cgatgttcctgttcgctgaaacaccgcacgcttacctgcaaggcgtggc gctggaagtgatggcaaactccgataacgtgctgcgtgcgggtctgacg cctaaatacattgatattccggaactggttgccaatgtgaaattcgaag ccaaaccggctaaccagttgttgacccagccggtgaaacaaggtgcaga actggacttcccgattccagtggatgattttgccttctcgctgcatgac cttagtgataaagaaaccaccattagccagcagagtgccgccattttgt tctgcgtcgaaggcgatgcaacgttgtggaaaggttctcagcagttaca gcttaaaccgggtgaatcagcgtttattgccgccaacgaatcaccggtg actgtcaaaggccacggccgtttagcgcgtgtttacaacaagctgtaa
```

The PMI-encoding synthetic DNA sequence with maize preferred codons (hereinafter "SynZmPMI," SEQ ID NO: 2) was obtained by reverse-translating the PMI protein sequence manually using the codons outlined in U.S. Pat. No. 6,075,185 to Koziel et al. Specifically, the following codons were used: Ala, GCC; Arg, CGC; Asn, AAC; Asp, GAC; Cys, TGC; Gln, CAG; Glu, GAG; Gly, GGC; His, CAC; Ile, ATC; Leu, CTG; Lys, AAG; Met, ATG; Phe, TTC; Pro, CCC; Ser, AGC; Thr, ACC; Trp, TGG; Tyr, TAC; and Val, GTG. A Kozak sequence (5'-GGCAGCAGCC-3') was added immediately upstream of the ATG start codon of the SynZmPMI gene. An additional stop codon (TAG) was added following the stop codon TGA. Also, two restriction sites, BamHI and SacI, were added to the 5'- and 3'-end of the Kozak-SynZmPMI sequences as cloning sites for ease of DNA manipulation. The final version is 1179 bp in length.

SynZmPMI

SEQ ID NO: 2

5'ATGCAGAAGCTGATCAACAGCGTGCAGAACTACGCCTGGGGCAGCAA

GACCGCCCTGACCGAGCTGTACGGCATGGAGAACCCCAGCAGCCAGCCC

ATGGCCGAGCTGTGGATGGGCGCCCACCCCAAGAGCAGCAGCCGCGTGC

AGAACGCCGCCGGCGACATCGTGAGCCTGCGCGACGTGATCGAGAGCGA

CAAGAGCACCCTGCTGGGCGAGGCCGTGGCCAAGCGCTTCGGCGAGCTG

CCCTTCCTGTTCAAGGTGCTGTGCGCCGCCCAGCCCCTGAGCATCCAGG

TGCACCCCAACAAGCACAACAGCGAGATCGGCTTCGCCAAGGAGAACGC

CGCCGGCATCCCCATGGACGCCGCCGAGCGCAACTACAAGGACCCCAAC

CACAAGCCCGAGCTGGTGTTCGCCCTGACCCCCTTCCTGGCCATGAACG

CCTTCCGCGAGTTCAGCGAGATCGTGAGCCTGCTGCAGCCCGTGGCCGG

CGCCCACCCCGCCATCGCCCACTTCCTGCAGCAGCCCGACGCCGAGCGC

CTGAGCGAGCTGTTCGCCAGCCTGCTGAACATGCAGGGCGAGGAGAAGA

GCCGCGCCCTGGCCATCCTGAAGAGCGCCCTGGACAGCCAGCAGGGCGA

GCCCTGGCAGACCATCCGCCTGATCAGCGAGTTCTACCCCGAGGACAGC

GGCCTGTTCAGCCCCCTGCTGCTGAACGTGGTGAAGCTGAACCCCGGCG

AGGCCATGTTCCTGTTCGCCGAGACCCCCCACGCCCTACCTGCAGGGCGT

GGCCCTGGAGGTGATGGCCAACAGCGACAACGTGCTGCGCGCCGGCCTG

ACCCCCAAGTACATCGACATCCCCGAGCTGGTGGCCAACGTGAAGTTCG

AGGCCAAGCCCGCCAACCAGCTGCTGACCCAGCCCGTGAAGCAGGGCGC

CGAGCTGGACTTCCCCATCCCCGTGGACGACTTCGCCTTCAGCCTGCAC

GACCTGAGCGACAAGGAGACCACCATCAGCCAGCAGAGCGCCGCCATCC

TGTTCTGCGTGGAGGGCGACGCCCACCCTGTGGAAGGGCAGCCAGCAGCT

GCAGCTGAAGCCCGGCGAGAGCGCCTTCATCGCCGCCAACGAGAGCCCC

GTGACCGTGAAGGGCCACGGCCGCCTGGCCCGCGTGTACAACAAGCTGT

GATAG-3'

The amino acid sequence encoded by the converted PMI gene remained the same as the original *E. coli* version (SEQ ID NO:3), while the converted DNA sequence shows 76% identity to the native sequence.

*E. coli* PMI amino acid sequence (SEQ ID NO: 3)

MQKLINSVQNYAWGSKTALTELYGMENPSSQPMAELWMGAHPKSSSRVQ

NAAGDIVSLRDVIESDKSTLLGEAVAKRFGELPFLFKVLCAAQPLSIQV

HPNKHNSEIGFAKENAAGIPMDAAERNYKDPNHKPELVFALTPFLAMNA

FREFSEIVSLLQPVAGAHPAIAHFLQQPDAERLSELFASLLNMQGEEKS

RALAILKSALDSQQGEPWQTIRLISEFYPEDSGLFSPLLLNVVKLNPGE

AMFLFAETPHAYLQGVALEVMANSDNVLRAGLTPKYIDIPELVANVKFE

AKPANQLLTQPVKQGAELDFTIPVDDFAFSLHDLSDKETTISQQSAAIL

FCVEGDATLWKGSQQLQLKPGESAFIAANESPVTVKGHGRLARVYNKL

This BamHI-Kozak-SynZmPMI-SacI sequence was synthesized and cloned into a plasmid vector to form pCR4SynPMI. The ZmUbi promoter was excised from pNOV 2117 (see U.S. Pat. No. 6,531,648 to Lanahan et al.) using HindIII/BamHI digestion, the synthetic PMI gene was excised from pCR4SynPMI using BamHI/SacI digestion, and these fragments were ligated by three-way ligation into pNOV 2804 digested with HindIII/SacI to form an expression cassette (SEQ ID NO:4).

prZmUbi-10 → cPMI-09 → tNOS-05-01

(SEQ ID NO: 4)

ctgcagtgcagcgtgacccggtcgtgcccctctctagagataatgagcattgcatgtctaagttataaaaaattaccacatatttttttgtcaca cttgtttgaagtgcagtttatctatctttatacatatatttaaactttactctacgaataatataatctatagtactacaataatatcagtgttttagagaa tcatatataaatgaacagttagacatggtctaaaggacaattgagtattttgacaacaggactctacagtttttatcttttttagtgtgcatgtgttctcctt ttttttttgcaaatagatcacctatataatacttcatccattttattagtacatccatttagggtttagggttaatggttatatagactaattttttttagtac atctattttattctattttagcctctaaattaagaaaactaaaactctattttagtttttttatttaataatttagatataaaatagaataaaataaagtgac taaaaattaaacaaataccattaagaaattaaaaaaactaaggaaacattttttcttgtttcgagtagataatgccagcctgttaaacgccgtcga cgagtctaacggacaccaaccagcgaaccagcagcgtcgcgtcgggccaagcgaagcagacggcacggcatctctgtcgctgcctctg gacccctctcgagagttccgctccaccgttggacttgctccgctgtcggcatccagaaattgcgtggcggagcggcagacgtgagccggc acggcaggcggcctcctcctcctctcacggcaccggcagctacggggattcctttcccaccgctccttcgctttcccttcctcgcccgccgt aataaatagacaccccctccacaccctattccccaacctcgtgttgttcggagcgcacacacacacaaccagatctcccccaaatccaccc gtcggcacctccgcttcaaggtacgcgctcgtcctccccccccccctctctaccttctctagatcggcgttccggtccatggttagggcc cggtagttctacttctgttcatgtttgtgttagatccgtgtttgtgttagatccgtgctgctagcgttcgtacacggatgcgacctgtacgtcagac acgttctgattgctaacttgccagtgtttctattggggaatcctgggatggctctagccgttccgcagacgggatcgatttcatgatttatttgttt cgttgcatagggtttggtttgccctttttccttttattcaatatgccgtgcacttgtttgtcgggtcatcttttcatgattttttagtcttggttgtgatga tgtggtctggttgggcggtcgttctagatcggagtagaattctgtttcaaactacctggtggatttattaattttggatctgtatgtgtgtgccatac atattcatagttacgaattgaagatgatggatggaaatatcgatctaggataggtatacatgttgatgcgggttttactgatgcatatacagagat -continued

```
gcttttgttcgcttggttgtgatgatgtggtgtggttgggcggtcgttcattcgttctagatcggagtagaatactgtttcaaactacctggtgtatt
tattaattaggaactgtatgtgtgtgtcatacatcttcatagttacgagtttaagatggatggaaatatcgatctaggataggtatacatgttgatgt
gggttttactgatgcatatacatgatggcatatgcagcatctattcatatgctctaaccttgagtacctatctattataataaacaagtatgttttata
attattttgatcttgatatacttggatgatggcatatgcagcagctatatgtggatttttttagccctgccttcatacgctatttatttgcttggtactgtt
tctttgtcgatgctcaccctgttgtttggtgttacttctgcagggatccggcagcagccatgcagaagctgatcaacagcgtgcagaactacg
cctggggcagcaagaccgccctgaccgagctgtacggcatggagaacccagcagccagcccatggccgagctgtggatgggcgccc
accccaagagcagcagccgcgtgcagaacgccgccggcgacatcgtgagcctgcgcgacgtgatcgagagcgacaagagcaccctg
ctgggcgaggccgtggccaagcgcttcggcgagctgcccttcctgttcaaggtgctgtgcgccgcccagccctgagcatccaggtgcac
cccaacaagcacaacagcgagatcggcttcgccaaggagaacgccgccgcatcccatggacgccgccgagcgcaactacaaggac
cccaaccacaagcccgagctggtgttcgccctgaccccatcctggccatgaacgccttccgcgagttcagcgagatcgtgagcctgctgc
agcccgtggccggcgcccacccgccatcgcccacttcctgcagcagcccgacgccgagcgcctgagcgagctgttcgccagcctgct
gaacatgcagggcgaggagaagagccgcgccctggccatcctgaagagcgccctggacagccagcagggcgagccctggcagacca
tccgcctgatcagcgagttctaccccgaggacagcggcctgttcagcccctgctgctgaacgtggtgaagctgaacccggcgaggcca
tgttcctgttcgccgagacccccacgcctacctgcagggcgtggccctggaggtgatggccaacagcgacaacgtgctgcgcgccggc
ctgaccccaagtacatcgacatccccgagaggtggccaacgtgaagttcgaggccaagcccgccaaccagctgctgacccagcccgt
gaagcagggcgccgagctggacttccccatccccgtggacgacttcgccttcagcctgcacgacctgagcgacaaggagaccaccatca
gccagcagagcgccgccatcctgttctgcgtggagggcgacgccaccctgtggaagggcagccagcagctgcagctgaagcccggcg
agagcgccttcatcgccgccaacgagagccccgtgaccgtgaagggccacggccgcctggcccgcgtgtacaacaagctgtgatagga
gctctagatccccgaatttccccgatcgttcaaacatttggcaataaagtttcttaagattgaatcctgttgccggtcttgcgatgattatcatataa
tttctgttgaattacgttaagcatgtaataattaacatgtaatgcatgacgttatttatgagatgggttttatgattagagtcccgcaattatacattt
aatacgcgatagaaaacaaaatatagcgcgcaaactaggataaattatcgcgcgcggtgtcatctatgttactagatc
```

Example 2

Transformation of Monocots with the Converted PMI Gene

The maize codon-optimized version of the PMI selectable marker gene was compared to the original bacterial PMI gene in the transformation of maize, rice (Indica and Japonica rice), and sugar cane. No apparent increase in transformation efficiency was seen in maize or in Japonica rice.

However, for Agrobacterium-mediated transformation of both sugar cane and Indica rice, transformation efficiency was improved by the maize codon-optimized version of the PMI selectable marker gene. This was unexpected because, in sugar cane, the bacterial gene was already very functional as a selectable marker, and when it was compared with biolistics-mediated transformation, a marked difference was not seen. In rice, this improvement was not seen in the Japonica cultivar, but an improvement was seen with an Indica rice cultivar.

I. Maize Transformation

Three independent maize transformation experiments were performed with the synthetic (maize-optimized) PMI gene including a Kozak sequence (Koz-syn PMI), and for the native PMI gene with (Koz-native PMI) and without (pNOV2117-native PMI) a Kozak sequence.

Transgenic maize events were produced by Agrobacterium-mediated transformation of the inbred corn (Zea mays) line A188. Transformation was accomplished essentially as described in Negrotto et al. (Plant Cell Reports 19: 798-803, 2000), incorporated herein by reference. Immature embryos were excised from 8-12 day old ears and rinsed with fresh medium in preparation for transformation. Embryos were mixed with the suspension of Agrobacterium cells harboring the transformation vector, vortexed for 30 seconds, and allowed to incubate for an additional 5 minutes. Excess Agrobacterium solution was aspirated and embryos were then moved to plates containing a non-selective culture medium. Embryos were co-cultured with the remaining Agrobacterium at 22° C. for 2-3 days in the dark. Embryos were transferred to culture medium supplemented with ticarcillin (100 mg/ml) and silver nitrate (1.6 mg/l) and incubated in the dark for 10 days. Embryos producing embryogenic callus were transferred to selection medium containing mannose.

Regenerated plantlets were tested by TAQMAN® PCR analysis for the presence of native PMI or maize optimized PMI gene, as well as for the absence of the antibiotic resistance spectinomycin (spec) gene. Plants positive for both transgenes, and negative for the spec gene, were transferred to the greenhouse for further propagation.

In all experiments, the Koz-native PMI and Koz-synPMI constructs gave higher transformation frequencies than the native PMI without the Kozak sequence (Table 1). Maize-optimization of the codons of PMI did not seem to affect transformation frequency.

TABLE 1

| Plasmid | No. of Embryos Used | Transformation Frequency* |
|---|---|---|
| pNOV2117-native PMI | 99 | 29.3 |
| Koz-native PMI | 89 | 62.9 |
| Koz-syn PMI | 92 | 55.4 |

*Percent of embryos used in transformation.

Addition of the Kozak sequence to the native or synthetic (maize-optimized) PMI sequence provided an increase in transformation efficiency.

Expression of PMI was analyzed by determining the levels of PMI mRNA and protein in transformed maize plants. The results of this analysis indicated that the mRNA levels paralleled the protein levels, with the native PMI and Kozak-native PMI being about the same, and the Kozak-synPMI being markedly higher (6.7-fold increase in protein in the leaves of maize) (Table 2).

TABLE 2

| Plasmid | PMI Transcript Levels Relative to Control (Average ± SE) | Average ng PMI/mg Soluble Protein |
|---|---|---|
| pNOV2117, native PMI | 4346.9 ± 1354.4 (N = 22) | 3.3 (N = 23) |
| Koz-native PMI | 2984.4 ± 616.6 (N = 37) | 2.4 (N = 40) |
| Koz-synPMI | 10519.6 ± 1525.6 (N = 43) | 15.8 (N = 46) |

N = number of events analyzed

The data did not provide insight as to why altering codon usage would result in an increase in steady state transcript and protein levels, or why the transformation frequency was consistently higher with the Kozak-native PMI constructs compared to the native PMI without Kozak, even though their PMI protein levels were about the same. Moreover, the data did not indicate why the transformation frequency was not different between the Kozak-nativePMI and the Kozak-synPMI when there were differences in transcript and protein levels.

For use in maize production, it is desirable that the plants have a low copy number of the transformed gene with no vector backbone DNA present. Accordingly, the total number of transformation events was determined, as were the low copy number, no backbone events. The results of this analysis are presented in Table 3. These results indicate that plants with a low copy number of the PMI gene and no vector backbone could be easily obtained.

TABLE 3

| Plasmid | Number of Events Analyzed | Transformation Frequency* Total Events | Transformation Frequency* Low Copy Number, No Vector Backbone |
|---|---|---|---|
| pNOV2117-native PMI | 69 | 33 | 22 |
| Koz-native PMI | 61 | 66 | 25 |
| Koz-synPMI | 65 | 66 | 37 |

*Percent of embryos used in transformation.

Again, however, there was no apparent increase in transformation frequency when the maize-optimized PMI was used as compared with the native PMI.

II. Rice Transformation

To determine whether similar trends were present in other monocots, rice transformation experiments were performed with the synthetic PMI gene including a Kozak sequence (Koz-synPMI), and for the native PMI gene with (Koz-native PMI) and without (pNOV2117-native PMI) a Kozak sequence.

Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about 2 days at 28° C. *Agrobacterium* is re-suspended in liquid MS-CIM medium. The *Agrobacterium* culture is diluted to an ($OD_{600}$ of 0.2-0.3 and acetosyringone is added to a final concentration of 200 uM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*.

Cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse ($T_o$ generation), grown to maturity, and the $T_1$ seed is harvested.

When analyzing the transformation frequency of Japonica rice, there was no detectable effect of the Kozak sequence or codon optimization on transformation frequency (Table 4).

TABLE 4

| Plasmid | No. of Embryos Used | Transformation Frequency (Average Events/ Gram DNA ± SD)* |
|---|---|---|
| pNOV2117-native PMI | 150 | 320 ± 161 |
| Koz-native PMI | 150 | 277 ± 30 |
| Koz-syn PMI | 150 | 320 ± 110 |

*Values are from 2 independent experiments.

However, the protein levels showed the same trend as in maize, with the native PMI and the Kozak-native PMI being relatively low, and the Kozak-synPMI sequence providing a 13.1-fold increase in PMI protein in the leaves of rice as compared to Kozak-native PMI (Table 5).

TABLE 5

| Plasmid | No. of Embryos Used | Average ng PMI/mg Soluble Protein* |
|---|---|---|
| pNOV2117, native PMI | 80 | 7.9 |
| 12384, Koz-native PMI | 55 | 2.8 |
| 12385, Koz-synPMI | 49 | 36.6 |

*Values are from 2 independent transformation experiments.

In similar experiments, Indica rice (Variety IR68897B) was transformed with Agrobacterium strains LBA4404 and EHA101. Briefly, embryogenic responses are initiated and/or cultures are established from mature seed by culturing on Callus Induction Medium (CIM medium) (MS basal salts, 4.3 g/liter; B5 vitamins (200×), 5 ml/liter; Sucrose, 20 g/liter; 2,4-D (1 mg/ml), 2 ml/liter; adjust pH to 5.8 with 1 N KOH; Phytagel, 7 g/liter. Initial stages of culture response or established culture lines are inoculated and co-cultivated with the Agrobacterium tumefaciens strain EHA101 (Agrobacterium) containing the desired vector construction. Agrobacterium is cultured from glycerol stocks on solid YPC medium (100 mg/L spectinomycin and any other appropriate antibiotic) for about two days at 28° C. Agrobacterium is re-suspended in liquid MS-D2 medium. The Agrobacterium culture is diluted to an $OD_{600}$ of 0.2-0.3 and acetosyringone is added to a final concentration of 400 uM. Acetosyringone is added before mixing the solution with the sugar cane cultures to induce Agrobacterium for DNA transfer to the plant cells. For inoculation, the plant cultures are immersed in the bacterial suspension. The liquid bacterial suspension is removed and the inoculated cultures are placed on co-cultivation medium and incubated at 22° C. for two days in the dark. The cultures are then transferred to MS-D2 medium with Ticarcillin (400 mg/liter) to inhibit the growth of Agrobacterium For constructs utilizing the PMI selectable marker gene (Reed et al., In Vitro Cell. Dev. Biol.-Plant 37:127-132) or Zea mays optimized PMI gene, cultures are transferred to selection medium containing Mannose as a carbohydrate source (MS with 1% Mannose, 400 mg/liter Ticarcillin), and cultured for 3-4 weeks in the dark. Resistant colonies are then transferred to regeneration induction medium (MS with no 2,4-D, 2 mg/L IAA, Zeatin, 200 mg/liter Ticarcillin, 1% Mannose and Phytagel, 2 g/liter) and grown in the dark for 14 days, and then moved to the light growth room for 14 days. Regenerated shoots with roots are transferred to GA-7's with maintenance medium (MS with no hormones and 2% sucrose, 200 mg/liter Ticarcillin) for 3-4 weeks and then moved to the greenhouse when they are large enough. Plants are transplanted to soil in the greenhouse (To generation), and grown to maturity.

The results indicated that the Kozak-synPMI had a transformation frequency exceeding that of the Kozak-native PMI independent of the Agrobacterium strain employed (Table 6). Therefore, transformation frequency in Indica rice was improved with synthetic PMI.

TABLE 6

| | Agrobacterium Strain LBA4404 | | Agrobacterium Strain EHA101 | |
|---|---|---|---|---|
| Plasmid | No. of Embryos Used | Transformation Frequency*[a] | No. of Embryos Used | Transformation Frequency*[b] |
| Koz-native PMI | 175 | 10.3 | 163 | 36.2 |
| Koz-synPMI | 175 | 22.3 | 163 | 49.7 |

Results are the average of 2 independent experiments.
*Percent of embryos used in transformation.
[a]Transformation frequency is based on transgenic shoots.
[b]Transformation frequency is based on transgenic callus.

III. Sugar Cane Transformation

Sugar cane transformation with the maize-optimized PMI selectable marker was also studied.

Embryogenic responses are initiated and/or cultures are established from sugar cane young leaves by culturing on SC-D2 medium (MS basal salts, 4.3 g/liter; B5 vitamins (200×), 5 ml/liter; Sucrose, 30 g/liter; 2,4-D (1 mg/ml), 2 ml/liter; adjust pH to 5.8 with 1 N KOH; Phytablend, 7 g/liter. Either mature embryos at the initial stages of culture response or established culture lines are inoculated and co-cultivated with the Agrobacterium tumefaciens strain EHA101 (Agrobacterium) containing the desired vector construction. Agrobacterium is cultured from glycerol stocks on solid YPC medium (100 mg/L spectinomycin and any other appropriate antibiotic) for about two days at 28° C. Agrobacterium is re-suspended in liquid MS-D2 medium. The Agrobacterium culture is diluted to an $OD_{600}$ of 0.3-0.4 and acetosyringone is added to a final concentration of 400 uM. Acetosyringone is added before mixing the solution with the sugar cane cultures to induce Agrobacterium for DNA transfer to the plant cells. For inoculation, the plant cultures are immersed in the bacterial suspension. The liquid bacterial suspension is removed and the inoculated cultures are placed on empty plate for co-cultivation and incubated at 22° C. for two days. The cultures are then transferred to SC-D2 medium with Ticarcillin (400 mg/liter) to inhibit the growth of Agrobacterium.

Cultures are transferred to selection medium containing Mannose as a carbohydrate source (MS with 0.8% Mannose, 400 mg/liter Ticarcillin), and cultured for 3-4 weeks in the dark. Resistant colonies are then transferred to regeneration induction medium (MS with no 2,4-D, 2 mg/L BAP, 200 mg/liter Ticarcillin, 0.6% Mannose) and grown in the dark for 7 days, and then moved to the light growth room for 14 days. Regenerated shoots are transferred to SC-Root-M6-T medium (MS with no hormones and 0.6% mannose, 200 mg/liter Ticarcillin) for 3-4 weeks and then moved to the greenhouse when they are large enough and have adequate roots. Plants are transplanted to soil in the greenhouse (To generation), and grown to maturity.

Two independent sugar cane transformation experiments were also performed with the synthetic PMI gene including a Kozak sequence (Koz-synPMI) and for the native PMI gene with a Kozak sequence (Koz-native PMI). In the first experiment, transformation frequency was analyzed. The results of this experiment indicated that the codon optimized PMI gene improved the transformation frequency of sugar cane (Table 7).

TABLE 7

| | Explants | | | |
|---|---|---|---|---|
| | Callus (2 Tillers) | | Callus (12 Grams)[b] | |
| Construct | Taqman | Transformation Frequency | Taqman | Transformation Frequency |
| Koz-native PMI | 5 | 2.5/tiller | 30 | 2.5 events/gram |
| Koz-synPMI | 20 | 10/tiller | 76 | 6.3 events/gram |

In the second experiment, transformation efficiency was determined for callus tissue transformed with the synthetic PMI and native PMI genes with Kozak sequences. The results of this experiment, as determined by the number of Cyano-Fluorescent protein (CFP) expressing callus lines, indicated that the transformation efficiency was improved by the codon optimized PMI gene (Table 8).

TABLE 8

| Construct | Explants (g) | CFP Callus Lines |
|---|---|---|
| Koz-native PMI | 10 | 33 |
| Koz-synPMI | 10 | 92 |

The regeneration of transgenic plants was subsequently determined. After a resting stage (i.e., a recovery period), explants were transferred to selection medium and then cultured at 28° C. in the dark for 3 weeks. Callus was then sub-cultured to regeneration medium and cultured for an additional 3 weeks with a light/dark cycle. The results of this analysis indicated that 25-30% of the callus transformed with the native PMI gene including a Kozak sequence generated shoots, whereas 50-80% of the callus transformed with the optimized PMI gene including a Kozak sequence generated shoots.

To expand the initial analysis, additional transformation experiments were carried out with the Koz-syn PMI construct (6 experiments) and Koz-native PMI construct (5 experiments). The results of this analysis are presented in Table 9 and further demonstrate that the codon optimized PMI gene generated 2- to 3-fold more transformation events than the native PMI gene in sugar cane cultivar L-97-128.

TABLE 9

| Construct | Callus Amount (g) | Taqman+ | Transformation Frequency (Events/g) |
|---|---|---|---|
| Koz-native PMI | 24 | 61 | 2.54 |
| | 23.5 | 107 | 4.55 |
| | 20 | 60 | 3 |
| | 22 | 36 | 1.64 |
| | 22 | 66 | 3 |
| Koz-synPMI | 12 | 76 | 6.3 |
| | 30 | 362 | 12.06 |
| | 10 | 96 | 9.6 |
| | 10 | 237 | 23.7 |
| | 14 | 127 | 9 |

The Koz-native PMI construct yielded a total of 330 TAQMAN® positive events, with an average transformation frequency of 2.96 events per gram of tissue. The Koz-syn PMI construct yielded at total of 898 TAQMAN® positive events, with an average transformation frequency of 11.82 events per gram of tissue. Thus, use of the maize-optimized PMI construct as a selectable marker for sugarcane transformation produced a 4-fold advantage over the native PMI construct in sugarcane.

Protein analysis indicated the same trend as in maize, with PMI expression in leaves being 20-fold higher (Table 10).

TABLE 10

| Construct | Number of Plants | Number of samples | ng PMI/mg Total Protein (Average ± SD) |
|---|---|---|---|
| pNOV2117-native PMI | 32 | 64 | 4.37 ± 2.29 |
| native PMI | 53 | 106 | 3.89 ± 2.13 |
| Koz-synPMI | 50 | 100 | 26.72 ± 26.33* |

*Large standard deviation due to variation of protein concentration from about 2 to greater than 100 ng PMI/mg of total protein.

Although the foregoing invention has been described in some detail by way of illustration and example for purposes of clarity and understanding, it will be clear to those of skill in the art that certain changes and modifications may be practiced within the scope of the appended claims.

What is claimed is:

1. A method for increasing the transformation frequency of a monocotyledonous plant tissue, comprising:
   introducing a heterologous nucleic acid comprising a coding region having one or more maize-optimized codons into a cell of said plant tissue, wherein said coding region comprises at least 500 consecutive nucleotides of SEQ ID NO:2, or said coding region comprises a nucleotide sequence having at least 95% sequence identity to SEQ ID NO:2, wherein said coding region codes for a phosphomannose isomerase (PMI) protein, thereby producing a transformed monocotyledonous cell comprising the nucleic acid;
   whereby said transformation frequency of said monocotyledonous plant tissue is increased as compared to a transformation efficiency without maize-optimized codons in said coding region of said nucleic acid.

2. The method of claim 1, wherein said introducing step is carried out by *Agrobacterium*-mediated transformation.

3. The method of claim 2, wherein said monocotyledonous plant tissue has a 1-, 2-, or 3-fold greater transformation frequency as compared to a transformation frequency without maize-optimized codons in said coding region of said nucleic acid.

4. The method of claim 2, wherein said monocotyledonous plant tissue has a transformation frequency by *Agrobacterium*-mediated transformation without maize-optimized codons of less than about 20%, 15%, 10%, or 5% as compared to a transformation frequency with maize-optimized codons in said coding region of said nucleic acid.

5. The method of claim 1, wherein said monocotyledonous plant tissue is maize, rice, wheat or barley tissue.

6. The method of claim 1, wherein said monocotyledonous plant tissue is tissue of sugar cane.

7. The method of claim 1, wherein said monocotyledonous plant tissue is an Indica variety of rice.

8. The method of claim 1, further comprising: selecting a multiple shoot culture comprising the transformed cell; growing the multiple shoot culture under conditions that promote shoot elongation to produce at least one transformed shoot; and growing the at least one transformed shoot.

9. A method of transforming sugar cane using a phosphomannose-isomerase (PMI) protein as a selectable marker, said method comprising:
  (a) introducing a heterologous nucleic acid comprising a phosphomannose-isomerase (PMI) protein coding region having one or more maize-optimized codons, said PMI coding region comprising at least 500 consecutive nucleotides of SEQ ID NO:2, or said coding region comprising a nucleotide sequence having at least 95% identity to SEQ ID NO:2, into a cell of sugar cane plant tissue to thereby produce a transformed sugar cane cell comprising the nucleic acid, wherein said introducing step is carried out by *Agrobacterium*-mediated transformation; and
  (b) regenerating a transformed plant from the transformed cell under conditions selective for PMI protein expression;
to produce said transformed sugar cane.

10. The method of claim 9, wherein said sugar cane has a 1-, 2-, or 3-fold greater transformation frequency as compared to transformation with an expression cassette comprising a nucleic acid comprising SEQ ID NO:1.

11. The method of claim 9, wherein the regenerating step comprises:
  selecting a multiple shoot culture comprising a transformed cell; growing the multiple shoot culture under conditions that promote shoot elongation to produce at least one transformed shoot; and growing the at least one transformed shoot.

* * * * *

SEQUENCE LISTING

```
<160> NUMBER OF SEQ ID NOS: 5

<210> SEQ ID NO 1
<211> LENGTH: 1176
<212> TYPE: DNA
<213> ORGANISM: Escherichia coli

<400> SEQUENCE: 1
atgcaaaaac tcattaactc agtgcaaaac tatgcctggg gcagcaaaac ggcgttgact      60
gaactttatg gtatggaaaa tccgtccagc cagccgatgg ccgagctgtg gatgggcgca     120
catccgaaaa gcagttcacg agtgcagaat gccgccggag atatcgtttc actgcgtgat     180
gtgattgaga gtgataaatc gactctgctc ggagaggccg ttgccaaacg ctttggcgaa     240 ctgccttttcc tgttcaaagt attatgcgca gcacagccac tctccattca ggttcatcca     300
aacaaacaca attctgaaat cggttttgcc aaagaaaatg ccgcaggtat cccgatggat     360
gccgccgagc gtaactataa agatcctaac cacaagccgg agctggtttt tgcgctgacg     420
cctttccttg cgatgaacgc gtttcgtgaa ttttccgaga ttgtctccct actccagccg     480
```

-continued
gtcgcaggtg cacatccggc gattgctcac tttttacaac agcctgatgc cgaacgttta 540
agcgaactgt tcgccagcct gttgaatatg cagggtgaag aaaaatcccg cgcgctggcg 600
attttaaaat cggccctcga tagccagcag ggtgaaccgt ggcaaacgat tcgtttaatt 660
tctgaatttt acccggaaga cagcggtctg ttctccccgc tattgctgaa tgtggtgaaa 720
ttgaaccctg gcgaagcgat gttcctgttc gctgaaacac cgcacgctta cctgcaaggc 780
gtggcgctgg aagtgatggc aaactccgat aacgtgctgc gtgcgggtct gacgcctaaa 840
tacattgata ttccggaact ggttgccaat gtgaaattcg aagccaaacc ggctaaccag 900
ttgttgaccc agccggtgaa acaaggtgca gaactggact tcccgattcc agtggatgat 960
tttgccttct cgctgcatga ccttagtgat aaagaaacca ccattagcca gcagagtgcc 1020
gccattttgt tctgcgtcga aggcgatgca acgttgtgga aaggttctca gcagttacag 1080
cttaaaccgg gtgaatcagc gtttattgcc gccaacgaat caccggtgac tgtcaaaggc 1140
cacggccgtt tagcgcgtgt ttacaacaag ctgtaa 1176

<210> SEQ ID NO 2
<211> LENGTH: 1179
<212> TYPE: DNA
<213> ORGANISM: Artificial
<220> FEATURE:
<223> OTHER INFORMATION: Synthetic PMI sequence with maize preferred codons
<400> SEQUENCE: 2
atgcagaagc tgatcaacag cgtgcagaac tacgcctggg gcagcaagac cgccctgacc 60
gagctgtacg gcatggagaa ccccagcagc cagcccatgg ccgagctgtg gatgggcgcc 120
caccccaaga gcagcagccg cgtgcagaac gccgccggcg acatcgtgag cctgcgcgac 180
gtgatcgaga gcgacaagag caccctgctg ggcgaggccg tggccaagcg cttcggcgag 240
ctgcccttcc tgttcaaggt gctgtgcgcc gcccagcccc tgagcatcca ggtgcacccc 300
aacaagcaca acagcgagat cggcttcgcc aaggagaacg ccgccggcat ccccatggac 360
gccgccgagc gcaactacaa ggaccccaac cacaagcccg agctggtgtt cgccctgacc 420
cccttcctgg ccatgaacgc cttccgcgag ttcagcgaga tcgtgagcct gctgcagccc 480
gtggccggcg cccaccccgc catcgcccac ttcctgcagc agcccgacgc cgagcgcctg 540
agcgagctgt tcgccagcct gctgaacatg cagggcgagg agaagagccg cgccctggcc 600
atcctgaaga gcgccctgga cagccagcag ggcgagccct ggcagaccat ccgcctgatc 660
agcgagttct accccgagga cagcggcctg ttcagccccc tgctgctgaa cgtggtgaag 720
ctgaaccccg gcgaggccat gttcctgttc gccgagaccc cccacgccta cctgcagggc 780
gtggccctgg aggtgatggc caacagcgac aacgtgctgc gcgccggcct gacccccaag 840
tacatcgaca tccccgagct ggtggccaac gtgaagttcg aggccaagcc cgccaaccag 900
ctgctgaccc agcccgtgaa gcagggcgcc gagctggact tccccatccc cgtggacgac 960
ttcgccttca gcctgcacga cctgagcgac aaggagacca ccatcagcca gcagagcgcc 1020
gccatcctgt tctgcgtgga gggcgacgcc accctgtgga agggcagcca gcagctgcag 1080
ctgaagcccg gcgagagcgc cttcatcgcc gccaacgaga gccccgtgac cgtgaagggc 1140
cacggccgcc tggcccgcgt gtacaacaag ctgtgatag 1179

<210> SEQ ID NO 3
<211> LENGTH: 391

```
<212> TYPE: PRT
<213> ORGANISM: Escherichia coli

<400> SEQUENCE: 3

Met Gln Lys Leu Ile Asn Ser Val Gln Asn Tyr Ala Trp Gly Ser Lys
1               5                   10                  15

Thr Ala Leu Thr Glu Leu Tyr Gly Met Glu Asn Pro Ser Ser Gln Pro
            20                  25                  30

Met Ala Glu Leu Trp Met Gly Ala His Pro Lys Ser Ser Ser Arg Val
        35                  40                  45

Gln Asn Ala Ala Gly Asp Ile Val Ser Leu Arg Asp Val Ile Glu Ser
    50                  55                  60

Asp Lys Ser Thr Leu Leu Gly Glu Ala Val Ala Lys Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys His Asn Ser Glu Ile Gly Phe Ala Lys Glu
            100                 105                 110

Asn Ala Ala Gly Ile Pro Met Asp Ala Ala Glu Arg Asn Tyr Lys Asp
        115                 120                 125

Pro Asn His Lys Pro Glu Leu Val Phe Ala Leu Thr Pro Phe Leu Ala
    130                 135                 140

Met Asn Ala Phe Arg Glu Phe Ser Glu Ile Val Ser Leu Leu Gln Pro
145                 150                 155                 160

Val Ala Gly Ala His Pro Ala Ile Ala His Phe Leu Gln Gln Pro Asp
                165                 170                 175

Ala Glu Arg Leu Ser Glu Leu Phe Ala Ser Leu Leu Asn Met Gln Gly
            180                 185                 190

Glu Glu Lys Ser Arg Ala Leu Ala Ile Leu Lys Ser Ala Leu Asp Ser
        195                 200                 205

Gln Gln Gly Glu Pro Trp Gln Thr Ile Arg Leu Ile Ser Glu Phe Tyr
    210                 215                 220

Pro Glu Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Glu Ala Lys Pro Ala Asn Gln Leu Leu Thr Gln
    290                 295                 300

Pro Val Lys Gln Gly Ala Glu Leu Asp Phe Pro Ile Pro Val Asp Asp
305                 310                 315                 320

Phe Ala Phe Ser Leu His Asp Leu Ser Asp Lys Glu Thr Thr Ile Ser
                325                 330                 335

Gln Gln Ser Ala Ala Ile Leu Phe Cys Val Glu Gly Asp Ala Thr Leu
            340                 345                 350

Trp Lys Gly Ser Gln Gln Leu Gln Leu Lys Pro Gly Glu Ser Ala Phe
        355                 360                 365

Ile Ala Ala Asn Glu Ser Pro Val Thr Val Lys Gly His Gly Arg Leu
    370                 375                 380

Ala Arg Val Tyr Asn Lys Leu
385                 390
```

<210> SEQ ID NO 4
<211> LENGTH: 3466
<212> TYPE: DNA
<213> ORGANISM: Artificial
<220> FEATURE:
<223> OTHER INFORMATION: Kozak-SynZmPMI expression cassette sequence

<400> SEQUENCE: 4

| | |
|---|---:|
| ctgcagtgca gcgtgacccg gtcgtgcccc tctctagaga taatgagcat tgcatgtcta | 60 |
| agttataaaa aattaccaca tatttttttt gtcacacttg tttgaagtgc agtttatcta | 120 |
| tctttataca tatatttaaa ctttactcta cgaataatat aatctatagt actacaataa | 180 |
| tatcagtgtt ttagagaatc atataaatga acagttagac atggtctaaa ggacaattga | 240 |
| gtattttgac aacaggactc tacagtttta tcttttagt gtgcatgtgt tctccttttt | 300 |
| ttttgcaaat agcttcacct atataatact tcatccattt tattagtaca tccatttagg | 360 |
| gtttaggggtt aatggttttt atagactaat tttttagta catctatttt attctatttt | 420 |
| agcctctaaa ttaagaaaac taaaactcta ttttagtttt tttatttaat aatttagata | 480 |
| taaaatagaa taaaataaag tgactaaaaa ttaaacaaat accctttaag aaattaaaaa | 540 |
| aactaaggaa acattttttct tgtttcgagt agataatgcc agcctgttaa acgccgtcga | 600 |
| cgagtctaac ggacaccaac cagcgaacca gcagcgtcgc gtcgggccaa gcgaagcaga | 660 |
| cggcacggca tctctgtcgc tgcctctgga cccctctcga gagttccgct ccaccgttgg | 720 |
| acttgctccg ctgtcggcat ccagaaattg cgtggcggag cggcagacgt gagccggcac | 780 |
| ggcaggcggc ctcctcctcc tctcacggca ccggcagcta cgggggattc ctttcccacc | 840 |
| gctccttcgc tttcccttcc tcgcccgccg taataaatag acacccccctc cacaccctct | 900 |
| ttccccaacc tcgtgttgtt cggagcgcac acacacacaa ccagatctcc cccaaatcca | 960 |
| cccgtcggca cctccgcttc aaggtacgcc gtcgtcctc cccccccccc cctctctacc | 1020 |
| ttctctagat cggcgttccg gtccatggtt agggcccggt agttctactt ctgttcatgt | 1080 |
| ttgtgttaga tccgtgtttg tgttagatcc gtgctgctag cgttcgtaca cggatgcgac | 1140 |
| ctgtacgtca gacacgttct gattgctaac ttgccagtgt ttctctttgg ggaatcctgg | 1200 |
| gatggctcta gccgttccgc agacgggatc gatttcatga ttttttttgt ttcgttgcat | 1260 |
| aggggtttggt ttgcccttt cctttatttc aatatatgcc gtgcacttgt ttgtcgggtc | 1320 |
| atcttttcat gcttttttttt gtcttggttg tgatgatgtg gtctggttgg gcggtcgttc | 1380 |
| tagatcggag tagaattctg tttcaaacta cctggtggat ttattaattt tggatctgta | 1440 |
| tgtgtgtgcc atacatattc atagttacga attgaagatg atggatggaa atatcgatct | 1500 |
| aggataggta tacatgttga tgcgggtttt actgatgcat atacagagat gcttttttgtt | 1560 |
| cgcttggttg tgatgatgtg gtgtggttgg gcggtcgttc attcgttcta gatcggagta | 1620 |
| gaatactgtt tcaaactacc tggtgtattt attaattttg gaactgtatg tgtgtgtcat | 1680 |
| acatcttcat agttacgagt ttaagatgga tggaaatatc gatctaggat aggtatacat | 1740 |
| gttgatgtgg gttttactga tgcatataca tgatggcata tgcagcatct attcatatgc | 1800 |
| tctaaccttg agtacctatc tattataata aacaagtatg ttttataatt attttgatct | 1860 |
| tgatatactt ggatgatggc atatgcagca gctatatgtg gatttttttta gccctgcctt | 1920 |
| catacgctat ttatttgctt ggtactgttt cttttgtcga tgctcaccct gttgtttggt | 1980 |
| gttacttctg cagggatccg gcagcagcca tgcagaagct gatcaacagc gtgcagaact | 2040 |

```
acgcctgggg cagcaagacc gccctgaccg agctgtacgg catggagaac cccagcagcc    2100
agcccatggc cgagctgtgg atgggcgccc accccaagag cagcagccgc gtgcagaacg    2160
ccgccggcga catcgtgagc ctgcgcgacg tgatcgagag cgacaagagc accctgctgg    2220
gcgaggccgt ggccaagcgc ttcggcgagc tgcccttcct gttcaaggtg ctgtgcgccg    2280
cccagcccct gagcatccag gtgcacccca acaagcacaa cagcgagatc ggcttcgcca    2340
aggagaacgc cgccggcatc cccatggacg ccgccgagcg caactacaag gaccccaacc    2400
acaagcccga gctggtgttc gccctgaccc ccttcctggc catgaacgcc ttccgcgagt    2460
tcagcgagat cgtgagcctg ctgcagcccg tggccggcgc ccaccccgcc atcgcccact    2520
tcctgcagca gcccgacgcc gagcgcctga gcgagctgtt cgccagcctg ctgaacatgc    2580
agggcgagga aagagccgc gccctggcca tcctgaagag cgccctggac agccagcagg    2640
gcgagccctg gcagaccatc cgcctgatca gcgagttcta ccccgaggac agcggcctgt    2700
tcagccccct gctgctgaac gtggtgaagc tgaaccccgg cgaggccatg ttcctgttcg    2760
ccgagacccc ccacgcctac ctgcagggcg tggccctgga ggtgatggcc aacagcgaca    2820
acgtgctgcg cgccggcctg acccccaagt acatcgacat ccccgagctg gtggccaacg    2880
tgaagttcga ggccaagccc gccaaccagc tgctgaccca gccgtgaag cagggcgccg    2940 agctggactt ccccatcccc gtggacgact tcgccttcag cctgcacgac ctgagcgaca    3000
aggagaccac catcagccag cagagcgccg ccatcctgtt ctgcgtggag ggcgacgcca    3060
ccctgtggaa gggcagccag cagctgcagc tgaagcccgg cgagagcgcc ttcatcgccg    3120
ccaacgagag ccccgtgacc gtgaagggcc acggccgcct ggcccgcgtg tacaacaagc    3180
tgtgatagga gctctagatc cccgaatttc cccgatcgtt caaacatttg gcaataaagt    3240
ttcttaagat tgaatcctgt tgccggtctt gcgatgatta tcatataatt tctgttgaat    3300
tacgttaagc atgtaataat taacatgtaa tgcatgacgt tatttatgag atgggttttt    3360
atgattagag tcccgcaatt atacatttaa tacgcgatag aaaacaaaat atagcgcgca    3420
aactaggata aattatcgcg cgcggtgtca tctatgttac tagatc                 3466

<210> SEQ ID NO 5
<211> LENGTH: 13
<212> TYPE: RNA
<213> ORGANISM: Artificial
<220> FEATURE:
<223> OTHER INFORMATION: Consensus Kozak sequence

<400> SEQUENCE: 5
gccgccrcca ugg                                                          13
```